United States Patent
Okita et al.

(10) Patent No.: US 9,271,521 B2
(45) Date of Patent: Mar. 1, 2016

(54) INHIBITOR FOR LIVER CANCER ONSET AND PROGRESS

(75) Inventors: Kiwamu Okita, Ube (JP); Isao Sakaida, Ube (JP); Yoshihiro Morinaga, Kawasaki (JP); Shoji Fujitani, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1044 days.

(21) Appl. No.: 11/165,217

(22) Filed: Jun. 24, 2005

(65) Prior Publication Data
US 2006/0004101 A1 Jan. 5, 2006

Related U.S. Application Data

(63) Continuation of application No. PCT/JP03/16208, filed on Dec. 18, 2003.

(30) Foreign Application Priority Data

Dec. 26, 2002 (JP) .................................. 2002-377803

(51) Int. Cl.
*A61K 31/198* (2006.01)
*A23L 1/305* (2006.01)
*A61P 1/16* (2006.01)
*A23K 1/16* (2006.01)

(52) U.S. Cl.
CPC ............. *A23L 1/3051* (2013.01); *A23K 1/1634* (2013.01); *A61K 31/198* (2013.01); *A23V 2002/00* (2013.01)

(58) Field of Classification Search
CPC ................... A23V 2002/00; A23V 2250/0626; A23V 2250/0628; A23V 2250/0654; A61K 31/198; A61K 2300/00; A61K 1/1634; A23L 1/3051
See application file for complete search history.

(56) References Cited

U.S. PATENT DOCUMENTS

| 2001/0033848 A1* | 10/2001 | Jacobson et al. ............... 424/401 |
| 2003/0092622 A1* | 5/2003 | Sato et al. ........................ 514/12 |
| 2004/0209282 A1* | 10/2004 | Ault-Riche et al. .............. 435/6 |
| 2004/0241232 A1* | 12/2004 | Brown et al. .................. 424/469 |

FOREIGN PATENT DOCUMENTS

| CN | 1056225 A | 11/1991 |
| EP | 1541141 | 6/2005 |
| FR | 2440194 | 5/1980 |

(Continued)

OTHER PUBLICATIONS

Swendseid et al., "The Effects of Test Doses of Leucine, Isoleucine or Valine on Plasma Amino Acid Levels," 1965, Am J Clin Nutr, vol. 17, pp. 317-321.*

(Continued)

*Primary Examiner* — Kortney L Klinkel
(74) *Attorney, Agent, or Firm* — Oblon, McClelland, Maier & Neustadt, L.L.P.

(57) ABSTRACT

The present invention provides a prophylactic or therapeutic agent, a pharmaceutical composition and a health-promoting food, which are used for human or other animal for the inhibition of the onset or progress of liver cancer, namely, an inhibitor of the onset or progress of liver cancer, which contains isoleucine, leucine and valine as active ingredients, wherein the weight ratio of isoleucine, leucine and valine is preferably 1:1.5 to 2.5:0.8 to 1.7 and the daily dose is 2.0 g to 50.0 g.

22 Claims, 1 Drawing Sheet

(56) References Cited

FOREIGN PATENT DOCUMENTS

| | | |
|---|---|---|
| GB | 2037161 | 7/1980 |
| GB | 2113524 | 8/1983 |
| JP | 02-172915 | 7/1990 |
| JP | 06-256186 | 9/1994 |
| JP | 08-067628 | 3/1996 |
| WO | WO 2004/019928 A1 | 3/2004 |

OTHER PUBLICATIONS

Meng et al. ("Prospective randomized control study on the effect of branched-chain amino acids in patients with liver resection for hepatocellular carcinoma" Aust. N.Z. J. Surg. 1999, 69, 811-815.).*
Yasuharu Imai et al, "Relation of Interferon Therapy and Hepatocellular Carcinoma in Patients with Chronic Hepatitis C", *Annals of Internal Medicine*, Jul. 15, 1998, vol. 129, No. 2, pp. 94-99.
John G. McHutchison et al, "Interferon Alfa-2b Alone or In Combination With Ribavirin As Initial Treatment For Chronic Hepatitis C", *The New England Journal of Medicine*, Nov. 19, 1998, vol. 339, No. 21, pp. 1485-1492.
J. Main et al, "A double blind, placebo-controlled study to assess the effect of famciclovir on virus replication in patients with chronic hepatits B virus infection", *Journal of Viral Hepatitis*, 1996, vol. 3, pp. 211-215.
Hiroko Oka et al, "Prospective Study of Chemoprevention of Hepatocellular Carbinoma with Sho-saiko-to (TJ-9)", *Cancer*, Sep. 1, 1995, vol. 76, No. 5, pp. 743-749.
Yasuji Arase et al, "The Long Term Efficacy of Glycyrrhizin in Chronic Hepatitis C Patients", *Cancer*, Apr. 15, 1997, vol. 79, No. 8, pp. 1494-1500.
Tetsuro Nishihira et al, "Feature Articles: Amino Acid Imbalances and Cancer Treatment", *JJPEN*, 1997, vol. 19, No. 3, pp. 195-199 (with attached English translation).
Fumie Kurokawa et al, "Cancer Cell Metabolism and Nutrition", *Japanese Journal of Nutritional Assessment*, 1992, vol. 9, No. 2, pp. 142-146 (with attached English translation).

Yasutoshi Muto et al, "Nutritional Treatment for Chronic Liver Failure—With Emphasis on Branched-Chain Amino Acid Supplementation Therapy", *Japan Medical Journal*, Oct. 1, 1983, vol. 3101, pp. 3-9, (with attached English translation).
Yasutoshi Muto et al, "Relationship between Serum Albumin Level and Prognosis in Patients with Liver Cirrhosis—Results of a Clinical Trial of Branched-chain Amino Acid Granule (BCAA-G) Supplements", *JJPEN*, 1995, vol. 17, No. 12 (with attached English translation).
Noriaki Okuse et al, "Effects of Long-term Administration of Branched-chain Amino Acid Preparation in Hepatic P-63 LEC Rats", *Acta Hepatologica Japonica*, 2002, 43 Supplement (2): A359 (with attached English translation).
S. Sato et al., *Heptalogy Research*, vol. 31, pp. 232-240 (2005).
Akiharu Watanabe, "Nutritional prevention of hepatocellular carcinoma", *Pharma Medica*, vol. 17, No. 3, 1999, pp. 177-189 (with English translation).
Takashi Tsukishiro, et al., "Nutritional assessment from the viewpoint of immune potential Effect of branched-chain amino acids on cytolytic activities of liver-associated lymphocytes in hepatocarcinogenesis", vol. 14, No. 4, 1997, pp. 395-400 with 1 additional page (with English translation).
Takashi Tsukishiro, et al., "Effect of branched-chain amino acids on the composition and cytolytic activity of liver-associated lymphocytes in rats", Journal of Gastroenterology and Hepatology, vol. 15, No. 8, 2000, pp. 849-859.
Office Action issued Feb. 21, 2014 in Korean Application No. 10-2011-7023122.
Daiki Habu, et al., "Effect of oral supplementation with branched-chain amino acid granules on serum albumin level in the early stage of cirrhosis: a randomized pilot trial", Hepatology Research, vol. 25, 2003, pp. 312-318.
Yoshimasa Saito, et al., "Effect of the Molar Ratio of Branched-Chain to Aromatic Amino Acids on Growth and Albumin mRNA Expression of Human Liver Cancer Cell Lines in a Serum-Free Medium", Nutrition and Cancer, vol. 39, No. 1, 2001, pp. 126-131.

* cited by examiner

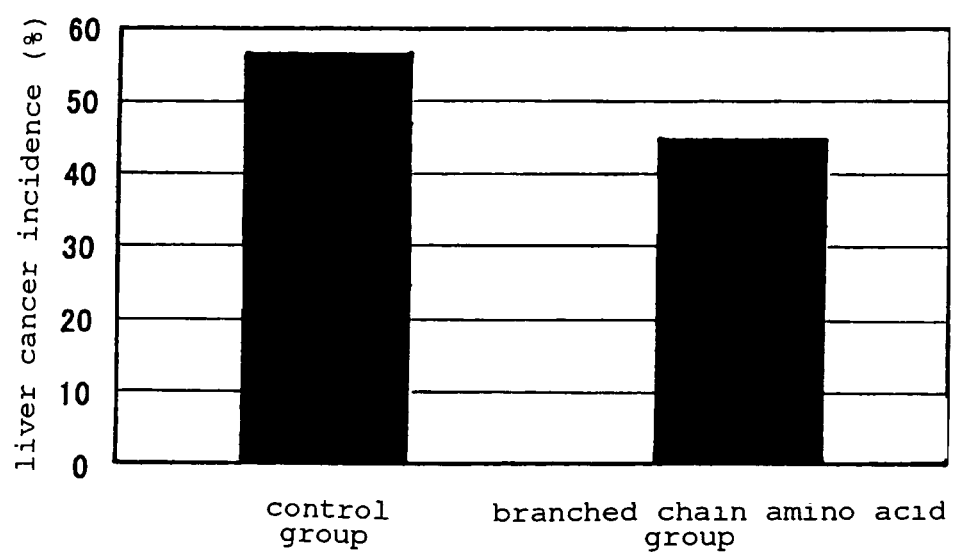

INHIBITOR FOR LIVER CANCER ONSET AND PROGRESS

CROSS REFERENCES TO RELATED APPLICATIONS

This application is a continuation of International Patent Application No. PCT/JP03/016208, filed on Dec. 18, 2003, and claims priority to Japanese Patent Application No. 2002-377803, filed on Dec. 26, 2002, both of which are incorporated herein by reference in their entireties.

BACKGROUND OF THE INVENTION

1. Field of the Invention

The present invention relates to pharmaceutical compositions which inhibit the onset or progress of liver cancer. Particularly, the present invention relates to pharmaceutical compositions which inhibit the onset or progress of liver cancer in patients with hepatitis or liver cirrhosis. The present invention also relates to health-promoting foods which are effective for inhibiting the onset or progress of liver cancer in patients with hepatitis or liver cirrhosis. The present invention further relates to methods for inhibiting the onset or progress of liver cancer by administering such a composition.

2. Discussion of the Background

The mechanism of the progress from hepatitis or liver cirrhosis to liver cancer has not been entirely elucidated. To inhibit liver cancer, however, it is considered important to remove the etiology of hepatitis or liver cirrhosis.

For example, it has been reported that removal of hepatitis virus by interferon treatment significantly inhibits carcinogenesis (*Ann. Intern. Med.*, vol. 129, p. 94 (1998)). As a method for removing hepatitis virus, a treatment using an antiviral drug can be mentioned (*N. Engl. J. Med.*, vol. 339, p. 1485 (1998) and *J. Viral Hepatitis*. vol. 3, p. 211 (1996)). In any event, it is not possible to remove the virus from all patients, and complete prophylaxis of liver cancer has not been achieved.

While attempts have been made to inhibit liver cancer by inhibiting chronic inflammation with a liver protecting agent and the like, liver cancer cannot be prevented entirely (*Cancer*, vol. 76, p. 743 (1995) and *Cancer*, vol. 79, p. 1494 (1997)).

Furthermore, while the treatment or inhibition of cancer by deficiency or excessive administration of particular amino acids, such as methionine deficiency, valine deficiency, aspartic acid deficiency, lysine deficiency, cystine deficiency, phenylalanine deficiency, increased administration of arginine, increased administration of glutamine and the like, has been also tried, the situation is by no means satisfactory (JJPEN (1997) 19:195-199 and "Japanese Journal of Nutritional Assessment" (1992) vol. 9 No. 2 p. 142-146).

Meanwhile, some patients with liver cirrhosis exhibit an accompanying decrease in blood Fischer ratio (branched chain amino acid mol (isoleucine+leucine+valine)/aromatic amino acid mol (phenylalanine+tyrosine)) and a decrease in serum albumin concentration, which are caused by an abnormality in the metabolism of protein and/or amino acid. The serum albumin concentration and Fischer ratio in these cases show a positive correlation (*Japan Medical Journal*, vol. 3101, p. 3 (1983)), and lower serum albumin concentration is known to cause shortened life expectancy (JJPEN (1995) 17:1135).

To improve hypoalbuminemia caused by disorders of amino acid metabolism in patients with liver cirrhosis, administration of a branched chain amino acid (BCAA) combination preparation called LIVACT (registered trademark) has been employed.

As for AMINOLEBAN EN (registered trademark), which is a nutritional status improving drug for patients with chronic hepatic failure associated with liver encephalopathy, it has been reported that administration of a feed containing this drug to rats with chemical-induced liver cancer revealed a tendency to inhibit liver cancer as compared to a control group bred on a conventional feed (Japanese Journal of Nutritional Assessment (1992) vol. 9 No. 2 p. 142-146). However, this reference does not at all suggest that such carcinogenesis inhibitory effect is related to a particular component in AMINOLEBAN EN (registered trademark), which is a balanced nutrition product containing carbohydrates, protein and fat, supplemented with various vitamins and minerals.

Similarly, it has been reported that long-term administration of a BCAA added feed to LEC rats (spontaneous carcinogenesis model) exhibited an inhibitory action on the progress of cancer, though the incidence of cancer did not vary from that of the control group (Acta Hepatologica Japonica (2002) 43 Supplement(2): A359). However, this reference does not describe the kind of BCAA, the mixing ratio and the like, nor does it suggest that such action is related to a particular component in BCAA.

The aforementioned LIVACT (registered trademark) is a preparation consisting of three kinds of branched chain amino acids of isoleucine, leucine, and valine, which was developed for the purpose of correcting the Fischer ratio, increasing serum albumin concentration and improving clinical conditions, by orally supplementing these branched chain amino acids at an appropriate ratio. However, its action to inhibit carcinogenesis is not known. The technical relationship between hypoalbuminemia and cancer onset has not been known, either.

Thus, there remains a need for compositions and methods for inhibiting the onset or progress of liver cancer

SUMMARY OF THE INVENTION

Accordingly, it is one object of the present invention to provide novel pharmaceutical compositions which inhibit the onset or progress of liver cancer.

It is another object of the present invention to provided novel pharmaceutical compositions which inhibit the onset or progress of liver cancer in patients with hepatitis or liver cirrhosis.

It is another object of the present invention to provide novel health-promoting foods which are effective for inhibiting the onset or progress of liver cancer in patients with hepatitis or liver cirrhosis.

It is another object of the present invention to provide novel methods for inhibiting the onset or progress of liver cancer by administering such a composition.

Thus, the problems to be solved by the present invention is the provision of a pharmaceutical composition for human and other animals, which is effective for the inhibition of the onset or progress of liver cancer, particularly, a pharmaceutical composition having an inhibitory effect on the onset or progress of liver cancer in patients with liver cirrhosis. It is another object of the present invention is to provide a novel method for the prophylaxis or treatment of liver cancer.

These and other objects, which will become apparent during the following detailed description, have been achieved by the inventors' discovery that compositions comprising three kinds of amino acids of isoleucine, leucine and valine as active ingredients have an inhibitory effect on the onset or progress of liver cancer, particularly on the onset or progress of liver cancer in patients with liver cirrhosis.

Thus, the present invention provides:

(1) A pharmaceutical composition for human or other animals for the inhibition of the onset or progress of liver cancer, which comprises three kinds of amino acids of isoleucine, leucine and valine.

(2) The pharmaceutical composition of (1), wherein the onset or progress of the aforementioned liver cancer is that in a patient with liver cirrhosis.

(3) The pharmaceutical composition of (1) or (2), wherein the weight ratio of isoleucine, leucine and valine is 1:1.5 to 2.5:0.8 to 1.7.

(4) The pharmaceutical composition of any of (1) to (3), whose daily dose is 2.0 g to 50.0 g.

(5) An inhibitor of the onset or progress of liver cancer, which comprises three kinds of amino acids of isoleucine, leucine and valine.

(6) The inhibitor of (5), wherein the aforementioned onset or progress of liver cancer is that in a patient with liver cirrhosis.

(7) The inhibitor of (5) or (6), wherein the weight ratio of isoleucine, leucine and valine is 1:1.5 to 2.5:0.8 to 1.7.

(8) The inhibitor of any of (5) to (7), whose daily dose is 2.0 g to 50.0 g.

(9) A method for the prophylaxis or treatment of liver cancer, which comprises administering an effective amount of three kinds of amino acids of isoleucine, leucine and valine to a patient.

(10) The method of (9), wherein the aforementioned onset or progress of liver cancer is that in a patient with liver cirrhosis.

(11) The method of (9) or (10), wherein the weight ratio of isoleucine, leucine and valine is 1:1.5 to 2.5:0.8 to 1.7.

(12) The method of any of (9) to (11), wherein the total of the daily doses of isoleucine, leucine and valine is 2.0 g to 50.0 g.

(13) Use of isoleucine, leucine and valine for the production of an inhibitor of the onset or progress of liver cancer, which comprises three kinds of amino acids of isoleucine, leucine and valine.

(14) The use of (13), wherein the aforementioned onset or progress of liver cancer is that in a patient with liver cirrhosis.

(15) The use of (13) or (14), wherein the isoleucine, leucine and valine are used at a weight ratio of 1:1.5 to 2.5:0.8 to 1.7.

(16) The use of any of (13) to (15), wherein a daily dose of the inhibitor of the onset or progress of liver cancer comprising three kinds of amino acids of isoleucine, leucine and valine is 2.0 g to 50.0 g.

(17) A commercial package comprising a pharmaceutical composition for human or other animals for the inhibition of the onset or progress of liver cancer, which comprises three kinds of amino acids of isoleucine, leucine and valine, and a written matter containing an explanation relating to the use for pharmaceutical application.

(18) A commercial package comprising an inhibitor of the onset or progress of liver cancer, which comprises three kinds of amino acids of isoleucine, leucine and valine, and a written matter containing an explanation relating to the use for pharmaceutical application.

(19) A health-promoting food comprising three kinds of amino acids of isoleucine, leucine and valine.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the cancer incidence of rats with liver cancer, which were fed with a choline deficient amino acid defined diet.

DETAILED DESCRIPTION OF THE PREFERRED EMBODIMENTS

The embodiment of the present invention is explained in the following.

The mode of administration and dosage form of the pharmaceutical composition of the present invention may be oral administration or parenteral administration, and as an agent for oral administration, solids such as powders, granules, capsules, tablets, chewable agents and the like and liquids such as solutions, syrups and the like can be mentioned, and as an agent for parenteral administration, injectable liquids, sprays and the like can be mentioned.

As animals other than human, domestic animals, domestic fowls and laboratory animals can be mentioned. For administration to animals other than human, addition of the composition to a feed is also possible.

In a package containing the pharmaceutical composition of the present invention and a written matter containing an explanation relating to the pharmaceutical use, as the written matter, what is called a package leaflet with explanation of use, efficacy, administration method and the like, and the like can be mentioned.

As the health-promoting food in the present invention, solid forms such as powders, granules, capsules, tablets, chewable agents and the like, which contain flavorings and/or sweeteners, or liquids such as solutions, syrups and the like can be mentioned, and further, dietary supplements to be added to confectioneries such as candy, cookies, cake and the like, and processed foods can be mentioned.

The disease states to which the pharmaceutical composition of the present invention is to be applied include liver diseases such as hepatitis, liver cirrhosis, liver cancer and the like, and the pharmaceutical composition is particularly effective for the prophylaxis of liver cancer in liver diseases such as hepatitis, liver cirrhosis and the like, which are associated with high risk of carcinogenesis, and inhibition of progress or cure of liver cancer for which conventional therapeutic agents for liver diseases failed to provide sufficient treatment effects.

In the application to these diseases, a decrease in the serum albumin level is not a requirement for the application.

The isoleucine, leucine and valine in the present invention may be D forms or L forms, or mixtures thereof, with preference given to L forms.

The mixing ratio of the three kinds of amino acids is 1:1.5 to 2.5:0.8 to 1.7, particularly preferably 1:1.9 to 2.2:1.1 to 1.3, by weight ratio. When the ratio is outside this range, significant action and effect are difficult to achieve.

While the dose may vary depending on the age, body weight, and condition of subject patients and the administration method, it generally includes dosages of isoleucine in an amount of 0.5 to 30.0 g per day, leucine in an amount of 1.0 to 60.0 g per day, and valine in an amount of 0.5 to 30.0 g per day. In the case of an ordinary adult, the dosage preferably includes isoleucine in an amount of 2.0 to 10.0 g per day, leucine in an amount of 3.0 to 20.0 g per day, and valine in an amount of 2.0 to 10.0 g per day, more preferably isoleucine in an amount of 2.5 to 3.5 g per day, leucine in an amount of 5.0 to 7.0 g per day, and valine in an amount of 3.0 to 4.0 g, per day. The total amount of the three amino acids is preferably about 2.0 g to 50.0 g per day, which is administered in 1 to 6, preferably 1 to 3, portions.

Isoleucine, leucine and valine, which are the active ingredients in the present invention, may be contained in separate preparations individually or in any combination, or all may be contained in one kind of preparation. For administration after individual processing into preparations, the administration routes and the administration dosage forms thereof may be the same or different, and the timing of the administration may be simultaneous or separate, which can be appropriately determined based on the kind of pharmaceutical agents to be concurrently used and the effect thereof.

In the present invention, the "weight ratio" means a ratio of the weight of each ingredient in the preparation. For example, when respective active ingredients of isoleucine, leucine and valine are contained in a single preparation, it means a ratio of the individual contents, and when each of the active ingredients, or any combination thereof is/are contained in plural preparations, it means a ratio of the weight of each active ingredient contained in each preparation.

In the present invention, the ratio of actual dose means the ratio of a single dose or a daily dose of each active ingredient per one subject of administration (i.e., patient). For example, when each active ingredient of isoleucine, leucine and valine is contained in a single preparation and administered to a subject of administration, the weight ratio corresponds to the dose ratio. When each active ingredient is contained separately or in any combination thereof in plural preparations and administered, the weight ratio corresponds to the ratio of the total amount of each active ingredient in each preparation administered at one time or in one day.

Isoleucine, leucine and valine have been widely used in the fields of pharmaceutical agents and food, and their safety has been established. For example, the acute toxicity ($LD_{50}$) of the pharmaceutical composition of the present invention containing these amino acids at a ratio of 1:2:1.2 is not less than 10 g/Kg when orally administered to mouse.

The pharmaceutical compositions of the present invention can be formulated into solids such as powders, granules, capsules, tablets, chewables and the like, liquids such as solutions, syrup and the like, or, injectable liquids, sprays and the like by conventional methods.

Where necessary for preparation, appropriate pharmacologically acceptable carriers, such as excipients, binders, lubricants, solvents, disintegrants, dissolution aids, suspending agents, emulsifiers, isotonicity agents, stabilizers, soothing agents, preservatives, antioxidants, corrigents, coloring agents and the like are mixed to give preparations.

As the excipient, organic excipients such as saccharides (e.g., lactose, glucose, D-mannitol, etc.), starches, celluloses (e.g., crystalline cellulose, etc.), and the like, inorganic excipients such as calcium carbonate, kaolin, and the like, and the like can be mentioned; as the binder, gelatinized starch, gelatin, gum arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, polyvinyl alcohol, and the like can be mentioned; as the lubricant, fatty acid salts such as stearic acid, stearate, and the like, talc, silicates, and the like can be mentioned; as the solvent, purified water, physiological brine, and the like can be mentioned: as the disintegrant, low substitution hydroxypropylcellulose, chemically modified cellulose, starches, and the like can be mentioned; as the dissolution aids, polyethylene glycol, propylene glycol, trehalose, benzyl benzoate, ethanol, sodium carbonate, sodium citrate, sodium salicylate, sodium acetate, and the like can be mentioned; as the suspending agent or emulsifier, sodium lauryl sulfate, gum arabic, gelatin, lecithin, glyceryl monostearate, polyvinyl alcohol, polyvinyl pyrrolidone, celluloses such as carboxymethylcellulose sodium, and the like, polysorbates, hydrogenated polyoxyethylene castor oil, and the like can be mentioned; as the isotonicity agent, sodium chloride, potassium chloride, saccharide, glycerine, urea, and the like can be mentioned; as the stabilizer, polyethylene glycol, sodium dextran sulfate, other amino acids, and the like can be mentioned; as the soothing agent, glucose, calcium gluconate, procain hydrochloride, and the like can be mentioned; as the preservative, paraoxybenzoic esters, chlorobutanol, benzyl alcohol, phenethyl alcohol, dehydroacetic acid, sorbic acid, and the like can be mentioned; as the antioxidant, subsulfate, ascorbic acid, and the like can be mentioned; as the corrigent, sweeteners, flavorings, and the like conventionally used in the fields of pharmaceutical agents and food can be mentioned; and as the coloring agent, artificial color conventionally used in the fields of pharmaceutical agents and food can be mentioned.

The pharmaceutical compositions of the present invention may contain other therapeutic drugs for liver diseases, such as interferon, glycyrrhizin, ursodeoxycholic acid, Ribavirin, Chinese medicine sho-saiko-to and the like.

These preparations can be administered by any administration method such as oral administration, injection or topical administration and the like.

In the present invention, the method for the prophylaxis or treatment of liver cancer includes inhibition of the onset or progress of liver cancer.

The health-promoting food includes health functional components that influence physiological function and biological activity in the body. The intake of the health-promoting food is expected to achieve a particular health object as compared to those taken in view of said health object by eating.

The health-promoting food may be sometimes referred to as a functional food, health food (including nutrient supplements) and the like. The functional food is a food prepared to utilize the function of a biologically regulating component contained in the food, and the health food generally refers to the food group considered to be useful for the promotion of health. The group includes nutrient supplements containing a particular nutrient as a main ingredient.

The health-promoting food of the present invention includes particular food for health and nutrient functional food, which can prevent the onset or progress of liver cancer in patients affected with hepatitis or liver cirrhosis, when taken as a daily dietary supplement.

A health-promoting food can be prepared by the same techniques used for pharmaceutical preparation similar to that for the aforementioned pharmaceutical compositions, or a technique for the preparation of general food. Furthermore, vitamins and other supplements may be added thereto.

Other features of the invention will become apparent in the course of the following descriptions of exemplary embodiments which are given for illustration of the invention and are not intended to be limiting thereof.

EXAMPLES

The present invention is explained in more detail by referring to the following Example. However, the following Example should be considered as an aid to obtain concrete understanding of the present invention, and the scope of the present invention is not at all limited by the following Example.

Example 1

6-week-old Fischer 344 rats were divided into two groups of a control group (N=30) and a branched chain amino acid group (N=28), and an experimental diet was freely given. As the experimental diet, a choline deficient amino acid defined diet+2.0% amino acid mixture (*) was given to the control group, and choline deficient amino acid defined diet+2.5% branched chain amino acid (**) defined diet (BCAA group) was given to the branched chain amino acid group.

At the time of death or at week 64 of administration, the rats were autopsied, the development or absence of liver cancer was histologically examined, and the cancer incidence was calculated. The results are as shown in FIG. 1.

The choline deficient amino acid defined diet was purchased from Dyets Inc. *; the ratio of each amino acid in the amino acid added mixture (*) was the same as the amino acid ratio of choline deficient diet of Dyets Inc. 2.0% amino acid mixture and 2.5% branched chain amino acid contained the same amount of nitrogen. ; In the branched chain amino acid (), the weight ratio of isoleucine:leucine:valine was 1:2:1.2.

As shown in FIG. 1, the cancer incidence of the rats with liver cancer, that were fed with a choline deficient amino acid defined diet, was remarkably lower in the branched chain amino acid group than in the control group, and it was clarified that the addition of the branched chain amino acid in the present invention was effective for the inhibition of the onset of cancer.

INDUSTRIAL APPLICABILITY

As mentioned above, the compositions which contain three kinds of branched chain amino acids of isoleucine, leucine and valine, which are provided by the present invention, inhibit the onset or progress of liver cancer, particularly, the onset or progress of liver cancer in patients with hepatitis or liver cirrhosis.

In addition, the pharmaceutical compositions of the present invention contain amino acids as active ingredients, are highly safe and almost free of side effects, and can be administered for a long time. Therefore, the compositions can be advantageously used for the prophylaxis or treatment over a long period up to the onset of liver cancer. In addition, it can be taken for a long time as a health-promoting food, and is effective for preventing the onset of liver cancer.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for treating liver cancer in a subject in need thereof, which comprises administering an effective amount of a therapeutic composition to said subject in need thereof, wherein said therapeutic composition consists of isoleucine, leucine, valine, one or more pharmacologically acceptable carrier, and, optionally, at least one additional drug for treating liver disease selected from the group consisting of an interferon, glycyrrhizin, ursodeoxycholic acid, Ribavirin, and Chinese medicine sho-saiko-to, wherein said isoleucine, leucine, and valine are administered in a weight ratio of 1:1.9 to 2.2:1.1 to 1.3, wherein said subject is a patient with liver cirrhosis, wherein said pharmacologically acceptable carrier is one or more excipient, binder, lubricant, solvent, disintegrant, dissolution aid, suspending agent, emulsifier, isotonicity agent, stabilizer, soothing agent, preservative, antioxidant, corrigent, coloring agent, or a mixture thereof, wherein said excipient is one or more excipient selected from the group consisting of a saccharide, a starch, a cellulose, calcium carbonate, and kaolin, wherein said stabilizer is selected from the group consisting of polyethylene glycol, and sodium dextran sulfate, and wherein said antioxidant is selected from the group consisting of subsulfate and ascorbic acid.

2. The method of claim 1, wherein said isoleucine, leucine and valine are administered in 1 to 6 portions daily.

3. The method of claim 2, wherein said treating liver cancer is inhibition of the progress of liver cancer.

4. The method of claim 1, wherein said isoleucine, leucine and valine are administered in 1 to 3 portions daily.

5. The method of claim 4, wherein said treating liver cancer is inhibition of the progress of liver cancer.

6. The method of claim 1, wherein said isoleucine is administered in an amount of 2.5 to 3.5 g per day, said leucine is administered in an amount of 5.0 to 7.0 g per day, and said valine is administered in an amount of 3.0 to 4.0 g per day, provided that said isoleucine, leucine, and valine are administered in a weight ratio of 1:1.9 to 2.2:1.1 to 1.3.

7. The method of claim 6, wherein said treating liver cancer is inhibition of the progress of liver cancer.

8. The method of claim 1, wherein said treating liver cancer is inhibition of the progress of liver cancer.

9. The method of claim 1, wherein said therapeutic composition is a dosage form for oral administration or for parenteral administration.

10. The method of claim 9, wherein said dosage form is a dosage form for oral administration and is selected from the group consisting of a powder, a granule, a capsule, a tablet, a chewable agent, a solution, and a syrup.

11. The method of claim 9, wherein said dosage form is a dosage form for parenteral administration and is selected from the group consisting of an injectable liquid and a spray.

12. The method of claim 1, wherein said binder is selected from the group consisting of gelatinized starch, gelatin, gum arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, and polyvinyl alcohol.

13. The method of claim 1, wherein said lubricant is selected from the group consisting of a fatty acid salt, talc, and a silicate.

14. The method of claim 1, wherein said solvent is selected from the group consisting of purified water and physiological brine.

15. The method of claim 1, wherein said disintegrant is selected from the group consisting of low substitution hydroxypropylcellulose, chemically modified cellulose, and a starch.

16. The method of claim 1, wherein said dissolution aid is selected from the group consisting of polyethylene glycol, propylene glycol, trehalose, benzyl benzoate, ethanol, sodium carbonate, sodium citrate, sodium salicylate, and sodium acetate.

17. The method of claim 1, wherein said suspending agent or emulsifier is selected from the group consisting of sodium lauryl sulfate, gum arabic, gelatin, lecithin, glyceryl monostearate, polyvinyl alcohol, polyvinyl pyrrolidone, a cellulose, a polysorbate, and hydrogenated polyoxyethylene castor oil.

18. The method of claim 1, wherein said isotonicity agent is selected from the group consisting of sodium chloride, potassium chloride, saccharide, glycerine, and urea.

19. The method of claim 1, wherein said soothing agent is selected from the group consisting of glucose, calcium gluconate, and procain hydrochloride.

20. The method of claim 1, wherein said preservative is selected from the group consisting of paraoxybenzoic esters, chlorobutanol, benzyl alcohol, phenethyl alcohol, dehydroacetic acid, and sorbic acid.

21. The method of claim 1, wherein said corrigent is a sweetener or a flavoring.

22. The method of claim 1, wherein said coloring agent is an artificial color.

\* \* \* \* \*